United States Patent [19]

Suh

[11] 4,442,240

[45] Apr. 10, 1984

[54] DENTAL FILLING MATERIALS

[75] Inventor: Byoung I. Suh, Glen Ellyn, Ill.

[73] Assignee: Bisco, Inc., Lombard, Ill.

[21] Appl. No.: 513,694

[22] Filed: Jul. 14, 1983

[51] Int. Cl.$^3$ .............................................. C08K 3/36
[52] U.S. Cl. ..................................... 523/116; 523/202;
523/203; 524/790; 106/308 Q; 428/405
[58] Field of Search ....................... 523/116, 202, 203;
524/790; 106/308 Q; 428/405

[56] References Cited

U.S. PATENT DOCUMENTS

| | | | |
|---|---|---|---|
| 3,194,784 | 7/1965 | Bowen | 523/166 |
| 3,272,772 | 9/1966 | Russell | 523/202 |
| 3,845,009 | 10/1974 | Gander | 523/116 |
| 4,362,842 | 12/1982 | Masuhara et al. | 523/116 |
| 4,412,015 | 10/1983 | Lustgarten et al. | 523/116 |

FOREIGN PATENT DOCUMENTS

| | | | |
|---|---|---|---|
| 47971 | 3/1982 | European Pat. Off. | 523/203 |
| 1278413 | 6/1972 | United Kingdom | 523/116 |

*Primary Examiner*—Lewis T. Jacobs
*Attorney, Agent, or Firm*—Merriam, Marshall & Bicknell

[57] ABSTRACT

An inorganic filler component for use in resin-based direct dental filling materials comprises fumed or submicron silica which has been silane treated and coated with a thin coating of an active polymerizable monomer of the type used as the binder in making the composition. The use of such a submicron material permits the total filler loading of the composition to be increased substantially, thereby increasing both the compressive and diametrical tensile strength of the cured material as well as improving its polishability and resistance to wear, and reducing its susceptibility to water absorption.

4 Claims, No Drawings

DENTAL FILLING MATERIALS

This invention relates to an improved inorganic filler material for use with a polymerizable monomer in preparing direct dental filling materials, and to a process for preparing the same.

BACKGROUND OF THE INVENTION

Direct dental filling materials consisting of a resin binder and a finely divided inorganic filler are well known to those skilled in the art. Since the disclosure of such materials in Bowen U.S. Pat. No. 3,066,112, variations and improvements thereon have been disclosed in U.S. Pat. Nos. 3,179,623; 3,194,783; 3,194,784; 3,835,090) and 3,926,906.

The dental filling materials to which the present invention pertains employ a resin binder system comprising a polyfunctional monomer having at least two acrylic end groups, as exemplified by 2,2-bis[4-(3-methacryloxy-2-hydroxy-propoxy)-phenyl]-propane (BIS-GMA) and other monomeric materials, as taught in the above-identified references, the disclosures of which are hereby incorporated by reference. Also preferably included in the resin system are other active monomers referred to by Bowen as reactive diluents, the function of which is to reduce the viscosity of the resin binder system.

For use as dental filling materials, the resin binder system, e.g., a mixture of BIS-GMA and a reactive diluent, is mixed with a large proportion, generally 65% by weight or more, of a finely divided inorganic filler material having a particle size within the range of about 1-85 microns, such as fused silica, crystalline quartz, aluminum oxide, and glass beads. There is also added to the mixture of the resin binder and the inorganic filler, an appropriate quantity of a free radical generating catalyst, such as benzoyl peroxide, and a suitable activator such as N,N-di-methyl-p-toluidine. The free radicals which are generated by the combination of the catalyst and the activator lead to rapid polymerization of the resin binder system, producing a dental filling material which has a desirable combination of properties, including high stiffness, high compressive strength, low shrinkage on hardening, and a low coefficient of thermal expansion, as known by those skilled in the art.

In the preparation of such dental filling materials, it is desirable to incorporate as high a proportion of inorganic filler as possible, in order to maximize the strength, rigidity and wear properties of the cured product. As a practical matter, however, it has been found that the use of more than about 75% of inorganic filler presents increasing difficulty, since the resulting paste material becomes non-homogenous and/or too stiff to be placed properly in a dental cavity and shaped to the desired contours, in accordance with the usual procedures employed with such dental filling materials.

It is also known in the prior art to pretreat the inorganic filler material with an ethylenically unsaturated organosilane finishing or keying agent, such as tris(2-methoxyethoxy) vinylsilane. Such treatment improves the bond between the organic polymer binder and the surface of the finely divided filler particles, thereby increasing the strength of the cured dental filling material, as well as making the filler desirably hydrophobic.

In addition to such fillers, used to impart the desired mechanical properties to the cured composite, it has also been suggested in U.S. Pat. No. 3,926,906 to incorporate a small proportion, typically 1-4% by weight of the total paste mixture, of sub-micron silica in order to prevent separation of the liquid phase of a paste mixture which might occur on storage

BRIEF DESCRIPTION OF THE INVENTION

In accordance with the invention, it has been found that the proportion of filler which can be incorporated in a direct dental filling composition can be increased by including as a portion of the filler, a substantial proportion of fumed or submicron silica which has been silane treated and coated with a thin coating of an active polymerizable monomer of the type used as the binder in making the composition. The use of such a submicron material permits the total filler loading of the composition to be increased substantially, thereby increasing both the compressive and diametrical tensile strength of the cured material as well as improving its polishability and resistance to wear, and reducing its susceptibility to water absorption.

DETAILED DESCRIPTION

In accordance with the invention, fumed or submicron silica, pretreated as hereinafter described, is used as a component of the filler in a direct dental filling material. Fumed silica is a known material consisting of amorphous, substantially dehydrated silica having a particle size less than about 0 05 microns and is commercially available in a number of different size ranges. As made, fumed silica is hydrophilic, although it can be made hydrophobic by suitable treatment. For purposes of this invention, only hydrophilic fumed silica can be used.

For use in the invention, fumed silica is first pretreated with an ethylenically unsaturated organosilane finishing or keying agent and then coated with an active polyfunctional polymerizable monomer having at least two acrylic end groups. The monomer used to coat the fumed silica may, but need not necessarily, be the same as the organic binder used in making the direct dental filling composition.

Silane treatment of the fumed silica is carried out by mixing the silica with a solution of the silane in a suitable non-aqueous solvent for both the silane as well as the polymerizable polyfunctional monomer, such as acetone, hexane or methanol, and agitating the mixture for a period of time, suitably 2-6 or preferably 4-5 hours, sufficient to insure the deposition of a layer of the silane on the surface of the silica. The silane solution will contain suitably about 2 to 40% and preferably 10 to 20% by weight of silane, based on the weight of the silica to be treated.

After a suitable period of agitation, there is added to the mixture of silica and solvent about 2 to 20% and preferably 5 to 15%, based on the weight of silica, of a polyfunctional monomer having at least two acrylic end groups. A preferred group of monomers includes those having a backbone structure including at least one aromatic ring and particularly those derived from bisphenol A by reaction with glycidyl methacrylate (BIS-GMA) or glycidyl acrylate. Other monomers which can be used are acrylic or methacrylic esters of an aliphatic diol or triol, e.g., as disclosed in U.S. Pat. No. 3,835,090. Mixtures of such monomers can also be used.

The mixture of silica and monomer-containing-solvent is then evaporated to dryness in any conventional manner at a temperature not exceeding 130° C, causing the deposition of the monomer as a surface coating on the silane-treated silica particles.

Although the use of a common solvent for both the silane and the polymerizable polyfunctional monomer, as described above, is preferred because of the simplified operating procedure which results, the invention is not restricted thereto. Alternatively, the silane-treated fumed silica can be made in any conventional manner, and thereafter coated and heat treated as described herein.

After evaporation of the solvent, the silica is subjected to a final heat-treating step at a temperature of 90°–130° C., and preferably 105°–120° C., for 1–5 and preferably 2–3 hours. The final heat treatment effectively dries the surface of the silica, which is then essentially free flowing and not sticky. Because of the great surface area of the fumed silica, the surface layer of resin is very thin. This coated material will hereinafter be referred to as "resin capped microsilica" or RCMS.

Resin capped microsilica can be used with conventional particulate inorganic filler materials heretofore known in an amount ranging from 2 to 90%, and preferably 10 to 50%, by weight of the total filler. Used in these proportions, RCMS increases the compressive and diametrical tensile strength of the cured dental filling material, as well as decreasing its ability to absorb water. In addition, the handling qualities, polishability and resistance to wear of the dental material are improved.

The advantages of the invention are illustrated in the following examples.

EXAMPLE 1

Preparation of Resin Capped Microsilica (RCMS)

100 grams of hydrophilic fumed silica (Aerosil OX-50, available from Degussa Co.) was added to a solution of 15 grams of γ-methacryloxypropyl-trimethoxy silane in 350 ml of acetone. The mixture was agitated for 4 hours and 5 grams of a monomeric resin mixture consisting of 70% BIS-GMA and 30% triethyleneglycol methacrylate (TriEDMA) was added. The mixture was stirred to dissolve the resin and the mixture was evaporated to dryness. The silica was then heat treated in air for 2.5 hours at 110° C. The resin-capped microsilica thus produced was generally free flowing, although a light grinding might have been desirable to break up any agglomeration which occurred.

EXAMPLE 2

Filler Loading

Using a mixture of BIS-GMA (70%) and tri-EDMA (30%) as the liquid phase, pastes were made with RCMS and finely divided quartz having a particle size of about 6 microns. In each case, filler was added to a fixed weight of resin until no more resin could be accommodated, as evidenced by insufficient wetting and/or the formation of lumps which would not disappear on continued stirring. The results are given in the following Table.

TABLE 1

| Filler | Maximum Filler % By Weight of Paste |
| --- | --- |
| RCMS alone | 65% |
| Quartz alone | 75% |
| Mixture of RCMS & Quartz containing 30% RCMS | 80% |

Strength Properties

Direct dental filling materials were prepared employing a resin comprising a mixture of BIS-GMA (70%) and tri-EDMA (30), filled with (i) high surface area acid-etched strontium glass powder (6.5 microns) alone, (ii) RCMS alone and (iii) a mixture of 30% RCMS and 70% strontium glass powder. The resins were cured with 0.6% of benzoylperoxide as catalyst and 0.3% of N,N-dihydroxyethyl-p-toluidine as initiator. After curing, compressive and diametrical tensile strength tests were performed. The results are given in Table 2 below.

TABLE 2

| Filler | Filler Loading, % of Paste | Compressive Strength | Diametrical Tensile Strength |
| --- | --- | --- | --- |
| RCMS | 64 | 37,000 psi | 365 kg/cm$^2$ |
| Strontium Glass | 78 | 37,000 psi | 460 kg/cm$^2$ |
| Mixture of RCMS and Strontium Glass, 30% RCMS | 82 | 50,000 psi | 600 kg/cm$^2$ |

The foregoing detailed description has been given for clearness of understanding only and no unnecessary limitations should be understood therefrom as modifications will be obvious to those skilled in the art.

What is claimed is:

1. A finely divided inorganic filler for use in preparing direct dental filling materials, said filler comprising organo-silane keying agent treated fumed silica having a surface coating comprising about 2-20%, based on the weight of the silica, of an active polyfunctional polymerizable monomer having at least two acrylic end groups.

2. A filler in accordance with claim 1 further including a finely divided organosilane keying agent treated inorganic filler having a particle size of about 1–85 microns in admixture with said fumed silica, said silica comprising about 2–90% by weight of said mixture.

3. A filler in accordance with claim 2 containing about 10–50% by weight of said fumed silica.

4. A method of treating fumed silica for use as a filler in direct dental filling materials comprising the steps of:
    treating said silica with an organosilane keying agent;
    forming on the surface of said silane-treated silica a coating of a polymerizable monomer having at least two acrylic end groups, said coating comprising about 2–20% by weight of the silica; and
    heat treating said coated silica at a temperature between 90° C. and 130° C. for 1 to 5 hours.

* * * * *